US006790519B1

(12) United States Patent
Johnson et al.

(10) Patent No.: US 6,790,519 B1
(45) Date of Patent: Sep. 14, 2004

(54) MOISTURE-INDUCED POLY(ETHYLENE OXIDE) GEL, METHOD OF MAKING SAME AND ARTICLES USING SAME

(75) Inventors: Eric D. Johnson, Larsen, WI (US); Gregory J. Wideman, Menasha, WI (US); James Hongxue Wang, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/579,842

(22) Filed: May 26, 2000

(51) Int. Cl.⁷ .......................... B32B 5/18; B32B 13/00; C08G 77/00
(52) U.S. Cl. .................. 428/303.4; 428/446; 521/154; 525/404
(58) Field of Search .............................. 428/304.4, 446; 521/154; 525/404, 288

(56) References Cited

U.S. PATENT DOCUMENTS

| | | | |
|---|---|---|---|
| 3,177,270 A | 4/1965 | Jones et al. |
| 3,323,978 A | 6/1967 | Rasmussen |
| 3,539,666 A | 11/1970 | Schirmer |
| 3,544,655 A | 12/1970 | Booth et al. |
| 3,666,737 A | 5/1972 | Lal et al. |
| 3,676,529 A | 7/1972 | Fall |
| 3,717,541 A | 2/1973 | Schirmer |
| 3,734,876 A | 5/1973 | Chu |
| 3,763,277 A | 10/1973 | Chu et al. |
| 3,830,888 A | 8/1974 | King |
| 3,833,708 A | 9/1974 | Miller et al. |
| 3,843,589 A | 10/1974 | Wartman |
| 3,862,266 A | 1/1975 | McConnell et al. |
| 3,868,433 A | 2/1975 | Bartz et al. |
| 3,891,584 A | 6/1975 | Ray-Chaudhun et al. |
| 3,933,943 A | 1/1976 | Fahrbach et al. |
| 3,935,141 A | 1/1976 | Potts et al. |
| 3,953,655 A | 4/1976 | Steinkamp et al. |
| 3,954,928 A | 5/1976 | Omori et al. |
| 3,957,605 A | 5/1976 | Assarsson et al. |
| 3,963,805 A | 6/1976 | Chu |
| 3,972,961 A | 8/1976 | Hammer et al. |
| 3,993,551 A | 11/1976 | Assarsson et al. |
| 4,018,729 A | 4/1977 | Faucher et al. |
| 4,021,509 A | 5/1977 | Murayama et al. |
| 4,029,720 A | 6/1977 | Seiler et al. |
| 4,080,405 A | 3/1978 | Agouri et al. |
| 4,102,845 A | 7/1978 | Schroder et al. |
| 4,200,704 A | 4/1980 | Stanley et al. |
| 4,206,155 A | 6/1980 | Korber |
| 4,225,650 A | 9/1980 | van Brederode et al. |
| 4,229,334 A | 10/1980 | Klabacka et al. |
| 4,528,334 A | 7/1985 | Knopf et al. |
| 4,619,988 A | 10/1986 | Leung et al. |
| 4,705,525 A | 11/1987 | Abel et al. |
| 4,705,526 A | 11/1987 | Abel et al. |
| 4,725,492 A | 2/1988 | Yazaki et al. |
| 4,792,477 A | 12/1988 | Ochiumi |

(List continued on next page.)

FOREIGN PATENT DOCUMENTS

| | | |
|---|---|---|
| AU | 52355/93 | 3/1994 |
| DE | 1806165 | 5/1969 |
| EP | 0184440 | 6/1986 |
| EP | 0210754 | 2/1987 |
| EP | 0 316 792 B1 | 5/1989 |
| EP | 0461785 | 12/1991 |
| EP | 0473091 | 3/1992 |
| EP | 0488119 | 6/1992 |
| EP | 0507561 | 10/1992 |
| EP | 0515949 | 12/1992 |
| EP | 0 590 965 | 4/1994 |
| EP | 0612773 | 8/1994 |
| EP | 0640650 | 3/1995 |
| EP | 0 687 689 | 12/1995 |
| EP | 0705934 | 4/1996 |
| EP | 0725090 | 8/1996 |
| GB | 2070046 | 9/1981 |
| GB | 2295553 | 6/1996 |

(List continued on next page.)

OTHER PUBLICATIONS

Furtura et al., Caplus An 1999:751417. abstract of JP11322812.*

Kuzuhara et al., Caplus An 1998:712708, abstract of JP10292084.*

Author:Mortensen, Kell et al. Title: Phase Behavior of Poly(propylene Oxide)–Poly(ethlene oxide)–Poly(propylene oxide) Triblock Copolymer Melt and Aqueous Solutions Publication:*Macromolecules* vol.–Issue:vol. 27, 20 pp.: pp. 5654–5666 Date: Jan. 1, 1994.

Author:Tang, Tao and Baotong Title: Compatibilization of Polypropylene/Poly(Ethylene Oxide) Blends and Crystallization Behavior of the Blends Publication:*Journal of Polymer Science: Part B: Polymer* vol.–Issue:32 pp. 1991–1992 Date: Jan. 1, 1994.

(List continued on next page.)

*Primary Examiner*—Jeffrey Mullis
(74) *Attorney, Agent, or Firm*—Brinks Hofer Gilson & Lione; G. Peter Nichols

(57) ABSTRACT

A method for making modified poly(ethylene oxide) by graft polymerizing thereto organic monomers containing a trialkoxy silane functional group or a moiety that reacts with water to form a silanol group, such as methacryloxypropyl trimethoxy silane, onto the poly(ethylene oxide) is disclosed. The graft polymerization is accomplished by mixing the poly(ethylene oxide), the silane-containing monomer(s) and an initiator and applying heat. Preferably, the method is a reactive-extrusion process. After graft polymerization, the modified poly(ethylene oxide) may be exposed or subjected to relatively high moisture conditions, thereby causing crosslinking and formation of a structure that is capable of absorbing relatively large amounts of saline. The resulting modified poly(ethylene oxide) has improved properties over articles similarly processed from unmodified poly(ethylene oxide).

24 Claims, No Drawings

U.S. PATENT DOCUMENTS

| | | |
|---|---|---|
| 4,810,612 A | 3/1989 | Ueda et al. |
| 4,840,851 A | 6/1989 | Golander et al. |
| 4,868,222 A | 9/1989 | Chau et al. |
| 4,874,540 A | 10/1989 | Greenwald et al. |
| 4,883,699 A | 11/1989 | Aniuk et al. |
| 5,011,892 A | 4/1991 | Engelhardt et al. |
| 5,041,496 A | 8/1991 | Engelhardt et al. |
| 5,059,630 A | 10/1991 | Fujita et al. |
| 5,075,061 A | 12/1991 | Howell |
| 5,095,619 A | 3/1992 | Davis et al. |
| 5,173,539 A | 12/1992 | Boocock et al. |
| 5,209,849 A | 5/1993 | Hu et al. |
| 5,217,798 A | 6/1993 | Brady et al. |
| 5,260,371 A | 11/1993 | Chen |
| 5,300,574 A | 4/1994 | Bacskai |
| 5,342,861 A | 8/1994 | Raykovitz |
| 5,346,959 A | 9/1994 | Goman |
| 5,354,618 A | 10/1994 | Ishigaki et al. |
| 5,360,419 A | 11/1994 | Chen |
| 5,360,586 A | 11/1994 | Wyatt et al. |
| 5,364,907 A | 11/1994 | Rolando et al. |
| 5,367,003 A | 11/1994 | Petcavich |
| 5,369,168 A | 11/1994 | Famili et al. |
| 5,382,703 A | 1/1995 | Nohr et al. |
| 5,385,974 A | 1/1995 | Ohmae |
| 5,391,423 A | 2/1995 | Wnuk et al. |
| 5,395,308 A | 3/1995 | Fox et al. |
| 5,412,029 A | 5/1995 | Elm et al. |
| 5,415,905 A | 5/1995 | Middlesworth et al. |
| 5,417,679 A | 5/1995 | Toms et al. |
| 5,429,874 A | 7/1995 | vanPutte |
| 5,444,123 A | 8/1995 | Zeltner et al. |
| 5,446,100 A | 8/1995 | Durrance et al. |
| 5,468,259 A | 11/1995 | Sheth et al. |
| 5,480,928 A | 1/1996 | Stratta |
| 5,489,470 A | 2/1996 | Noda |
| 5,489,647 A | 2/1996 | Kussmaul |
| 5,498,692 A | 3/1996 | Noda |
| 5,498,785 A | 3/1996 | Wang et al. |
| 5,509,913 A | 4/1996 | Yeo |
| 5,532,066 A | 7/1996 | Latiolais et al. |
| 5,540,663 A | 7/1996 | Kroner et al. |
| 5,541,259 A | 7/1996 | Doi |
| 5,549,791 A | 8/1996 | Herron et al. |
| 5,587,434 A | 12/1996 | McCullough, Jr. et al. |
| 5,674,578 A | 10/1997 | Giori |
| 5,700,872 A | 12/1997 | Wang et al. |
| 5,753,169 A | 5/1998 | Kaito et al. |
| 5,807,930 A | 9/1998 | Wang et al. |
| 5,952,433 A | 9/1999 | Wang et al. |

FOREIGN PATENT DOCUMENTS

| | | |
|---|---|---|
| JP | 49-126742 | 12/1974 |
| JP | 60195151 | 10/1985 |
| JP | 61-181859 | 8/1986 |
| JP | 61-272217 | 12/1986 |
| JP | 1-246111 A | 10/1989 |
| JP | 5-309111 | 11/1993 |
| JP | 8-212995 A | 8/1996 |
| JP | 10292084 | * 11/1998 |
| JP | 11322812 | * 11/1999 |
| WO | WO 94/00163 | 1/1994 |
| WO | WO 94/00293 | 1/1994 |
| WO | WO 95/11929 | 5/1995 |
| WO | WO 95/20614 | 8/1995 |
| WO | WO 95/20615 | 8/1995 |
| WO | WO 95/20621 | 8/1995 |
| WO | WO 95/23249 | 8/1995 |
| WO | WO 95/23250 | 8/1995 |
| WO | WO 96/20738 | 7/1996 |
| WO | WO 96/20831 | 7/1996 |
| WO | WO 96/21057 | 7/1996 |
| WO | WO 96/21475 | 7/1996 |

OTHER PUBLICATIONS

Author:Hu, Guo–Hua, et Title: Free Radical Grafting of Chemically Activated Maleic anhydride onto Polypropylene by Reactive Extrusion—abstract only Publication:*Annu. Tech. Conf.* —*Soc. Plast. Eng.* vol.–Issue:3 pp.: pp. Date: Jan. 1, 1994.

Author:Deng, Yulin et al. Title: Synthesis of Nonionic Flocculants by Gamma Irradiation of Mixtures of Polyacrylamide and Poly(ethylene oxide) Publications:*J. Applied Polymer Science* vol.–Issue:54 pp. 805–813 Date: Jan. 1, 1994.

Author:Liang, W. et al. Title: Use of Water Soluble Polymers for the Control of Rheology of Latex Dispersions Publication:Polm mater sci eng proc acs div polym mater sci eng vol.–Issue:66 pp. 75–76 Date: Jan. 1, 1992.

Author:Bromley, C.W.A. Title: The Preparation of Sterically Stabilised Aqueous Latices Using Polyethylene Oxide Publication:*Colloids and Surfaces* vol.–Issue:17 pp. 1–11 Date: Jan. 1, 1986.

Author:Lindstrom, T. et al. TItle: Network Flocculation and Fractionation of Latex Particles by Means of Polyethyleneoxide—Phenolformaldehyde Resin Complex Publication:*J. Colloid Interf Sci* vol.–Issue:97(1) pp.:62–67 Date: Jan. 1, 1984.

Author: Title: ASTM Designation: E 96–80, "Standard Test Methods for Water Vapor Transmission of Materials," Publication: vol.–Issue: pp.: pp. 742–775 Date: Jan. 1, 1981.

Heath, D. et al., "Rheological Investigations of the Effect of the Addition of Free Polymer to Concentrated Sterically Stabilised Polystyrene Latex Dispersions", *Faraday Discussions of the Chemical Society: Concentrated Colloidal Dispersions*, The Faraday Division, The Royal Society of Chemistry, London, UK, No. 76, 1983, pp. 203–218.

Bartczak, Z. et al., "Changes in Interface Shape During Crystallization in Two–Component Polymer Systems", *Polymer*, vol. 27, Apr. 1986,pp. 544–548.

Baker, J. A. et al., "Investigation of the Adsorption Configuration of Poly(ethylene oxide) and Its Copolymers with Poly(propylene oxide) on Model Polystyrene Latex Dispersions", *Langmuir—The ACS Journal of Surfaces and Colloids*, vol. 4, No. 4, Jul./Aug. 1988, pp. 1055–1061.

Tucker, P.S. et al., "Molecular Weight Effects on Phase Behavior of Blends of Poly(phenylene oxide) with Styrenic Triblock Copolymers", *Macromolecules*, vol. 21, 1988, pp. 2794–2800.

Callais, P. et al., "The Maleic Anhydride Grafting of Polypropylene with Organic Peroxides", *Proceedings of the Second International Congress on Compatibilizers and Reactive Polymer Alloying: Compalloy '90, Mar. 7–9, 1990, The Westin Canal Place Hotel, New Orleans, Louisiana*, Schotland Business Research, Inc., Princeton, NJ, Copyright: 1989, pp. 359–367.

Goodwin, J.V. et al., "Synthesis Characterization, and Rheology of Polymer–Stabilized Acqueous Suspensions of Polystyrene Latex", *Polymeric Materials: Science and Engineering*, American Chemical Society, vol. 61, 1989, pp. 156–160.

Oun, A.., "Preparation and Characterization of Polymer Stabilized Polystyrene Latex", *Polymer International*, vol. 29, 1992, pp. 313–318.

Song, Z. et al., "Melt Grafting of T–Butylaminoethyl Methacrylate Onto Polyethylene", *Polymer*, vol. 33, No. 15, 1992, pp. 3266–3273.

Liang, W. et al., "Effect of vol. Fraction and Particle Size on Depletion Flocculation of a Sterically Stabilized Latex Dispersion Induced by Addition of Poly (ethylene oxide)", *Journal of Colloid and Interface Science*, vol. 155, 1993, pp. 156–164.

American Society for Testing and Materials, "Standard Test Method for Tear–Propagation Resistance of Plastic Film and Thin Sheeting by a Single–Tear–Method", *American Society for Testing and Materials Standard, Designation: D 1938–1994*, ASTM, West Conshohocken, PA, Copyright: Apr. 1994, pp. 480–482.

Chern et al., "Emulsion Polymerization of Acrylic Monomers Stabilized by Poly (Ethylene oxide)", *Journal of Macromolecular Science—Pure and Applied Chemistry*, vol. 33, Nos. 7–12, 1996, pp. 1063–1075.

American Society for Testing and Materials, "Standard Test Method for Tensile Properties of Plastics", *American Society for Testing and Materials Standard, Designation: D 638–99*, ASTM, West Conshohoken, PA, Copyright: Feb. 2000, pp. 46–58.

* cited by examiner

MOISTURE-INDUCED POLY(ETHYLENE OXIDE) GEL, METHOD OF MAKING SAME AND ARTICLES USING SAME

FIELD OF THE INVENTION

The present invention is directed to a method of modifying poly(ethylene oxide). More particularly the present invention is directed to modified poly(ethylene oxide) that crosslinks upon exposure to moisture and is also melt processable. The present invention also relates to articles made from modified poly(ethylene oxide) that are capable of absorbing relatively large amounts of fluid.

BACKGROUND OF THE INVENTION

Disposable personal care products, such as pantiliners, diapers, tampons etc., are a great convenience. Such products provide the benefit of one time, sanitary use and are convenient because they are quick and easy to use. However, disposal of such products is a concern due to limited landfill space. Incineration of such products is not desirable because of increasing concerns about air quality and the costs and difficulties associated with separating such products from other disposed, non-incineratable articles. Consequently, there is a need for biodegradable personal care products.

Poly(ethylene oxide) ("PEO") is one of a very few polymers that is both water-soluble and thermally processable. PEO has also been shown to be biodegradable under a variety of conditions. Initial work was done with PEO N-80 (molecular weight ~200.000) which is commercially available from Union Carbide. This grade of PEO is suitable for extrusion processing into film. However, the resultant films have relatively low tensile strength. Ions ductility, and brittleness. Typical values are 12 MPa break stress and elongation at break of 220%. In an unmodified form, high molecular weight PEO is not thermally processable. Melt fracture and excessive vaporization are observed as PEO is extruded. The resulting resins cannot be cast into thin films and do not have properties that are useful for personal care applications.

A key requirement to achieve a substantially biodegradable personal care product, such as a diaper is to identify and utilize a biodegradable absorbent material that provides the expected levels of leakage protection. There is a wide variety of biodegradable polymers with the potential to become a functional absorbent, but in the current state of development, none provide the leakage protection of sodium polyacrylates. However, sodium polyacrylates are not appreciably degraded in mixed microbial systems unless they are so low in molecular weight (500–700 g/mol) that they are not functional as absorbents.

Consequently, there is a need for biodegradable, absorbent personal care products that are made from materials that can be relatively easily processed, such as by thermal processing, so that it can be easily fabricated into a wide range of structures, such as films, foams, and fibrous webs. Currently available water-soluble resins are not practical for melt processing thin films or fibers for personal care applications. What is needed in the art, therefore, is a water soluble resin that overcomes the difficulties associated with melt processing while also possessing good saline absorption characteristics and functional forms made therefrom are still absorbent, flexible and biodegradable. Examples of water-soluble resins include poly(alkylene oxides) such as PEO; poly(ethylene glycols), block copolymers of ethylene oxide and propylene oxide, poly(vinyl alcohol) or poly(alkyl vinyl ethers).

SUMMARY OF THE INVENTION

The present invention is directed to methods for improving saline absorption characteristics of functional forms made from the silane craft modified PEO of the present invention while maintaining the melt processability of silane graft modified PEO as quell as the softness and flexibility of personal care products made therefrom. More particularly, the present invention relates to methods of modifying PEO to improve its saline absorption characteristics while retaining its melt processability by grafting organic monomers containing trialkoxy silane functional groups, such as methacryloxypropyl trimethoxy silane, or a moiety that reacts with water to form a silanol group, onto the PEO. The grafting is accomplished by combining PEO; silane-containing monomer(s), an initiator and applying heat. In a preferred embodiment, the method of modification is a reactive-extrusion process. PEOs modified in accordance with this invention have improved water absorption characteristics and melt processabilities and can be thermally processed into films, fibers, foams and other articles which have improved properties over films, fibers, foams and articles similarly processed from unmodified PEO compositions.

To overcome the disadvantages of the prior art, this invention teaches a method of grafting trialkoxy silane functional group-containing organic monomers or monomers containing a moiety that reacts with water to form a silanol group, onto PEO in the melt. Modification of PEO produces a polymer that does not crosslink during melt processing, but rather can be processed into functional forms, such as fibers, films, foams and the like. Yet, when these functional forms made from the modified polymer of the present invention are exposed or subjected to relatively high moisture conditions, they crosslink with each other and form a gel that is capable of absorbing relatively large amounts of saline. Additionally, modified PEO resins in accordance with the present invention can be solidified into pellets for later thermal processing into useful shapes, such as films, fibers, foams and other useful forms which are in turn useful as components in personal care products. The resulting personal care products are soft and flexible and biodegradable.

As used herein, the term "graft copolymer" means a copolymer produced by the combination of two or more chains of constitutionally or configurationally different features, one of which serves as a backbone main chain, and at least one of which is bonded at sonic point(s) along the backbone and constitutes a side chain. As used herein, the term "grafting" means the forming of a polymer by the bonding of side chains or species at some point(s) along the backbone of a parent polymer. (See Sperling, L. H., *Introduction to Physical Polymer Science* 1986 pp. 44–47 which is incorporated by reference herein in its entirety.)

Modification of PEO resins with starting molecular weights of between about 3,350 g/mol and 8,000,000 g/mol are useful in the present invention. Modification of PEO resins with starting molecular weights of between about 300,000 g/mol to about 8,000,000 g/mol allows the modified PEO resins to be drawn into films with thicknesses of less than about 0.5 mil. Modification of PEO resins with starting molecular weights of between about 400,000 g/mol to about 8,000,000 g/mol is preferred for filmmaking. Films drawn from the modified PEO compositions have better softness, flexibility, and greater clarity than films drawn from unmodified low molecular weight PEO. Thermal processing of films from high molecular weight PEO modified in accordance with this invention also results in films with improved mechanical properties over films similarly processed from unmodified low molecular weight PEO films.

Modification of PEO resins with starting molecular weights of between about 50,000 g/mol to about 400,000 g/mol allows the modified PEO resins to be extruded into fibers using conventional melt spinning processes. Modification of PEO resins with starting molecular weights of between about 50,000 g/mol to about 200,000 g/mol is preferred for fiber making. The modification of PEO in accordance with this invention improves the melt properties of the PEO allowing the modified PEO to be melted and attenuated into fibers. Thus, the modified PEO can be processed into water-absorbent fibers using both meltblown and spunbond processes which are useful for liners, cloth-like outer covers, etc. in flushable personal products. The modified PEO can be processed into water-absorbent staple fibers for use in bonded carded webs or in airlaid structures.

These and other features and advantages of the present invention will become apparent after a review of the following detailed description of the disclosed embodiments and the appended claims.

DETAILED DESCRIPTION OF THE DISCLOSED EMBODIMENTS

The present invention comprises a grafted PEO that, upon exposure to moisture, crosslinks into a gel structure capable of absorbing relatively large amounts of fluids, such as water or saline. In accordance with the present invention, PEO is graft polymerized with an organic moiety capable of graft polymerization with PEO which moiety contains a trialkoxy silane functional group or which moiety reacts with water to form a silanol group. The silane graft modified PEO resin can be thermally processed into functional forms, such as films, fibers and foams. When these functional forms are exposed to moisture, a crosslinking reaction occurs, by the mechanism shown below, to provide a gel structure capable of absorbing relatively large amounts of water, such as more than 20 grams of saline per gram of polymer under free swell conditions.

Water-soluble polymers useful in the present invention include, but are not limited to, poly(alkylene oxides), such as poly(ethylene oxide) ("PEO"), poly(ethylene glycols), block copolymers of ethylene oxide and propylene oxide, poly(vinyl alcohol) and poly(alkyl vinyl ethers). These water-soluble polymers must be capable of graft polymerization with an organic moiety containing a trialkoxy silane functional group or a moiety that reacts with water to form a silanol group. The preferred water-soluble polymer for use in the present invention is PEO. The process for the graft polymerization of PEO with methacryloxypropyl trialkoxy silane followed by cross-linking upon exposure to moisture is shown below.

Graft Polymerization of PEO with Methacryloxypropyl Trialkoxy Silane Followed by Exposure to Moisture

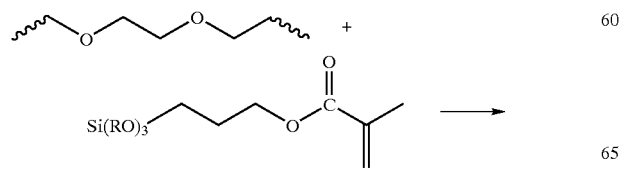

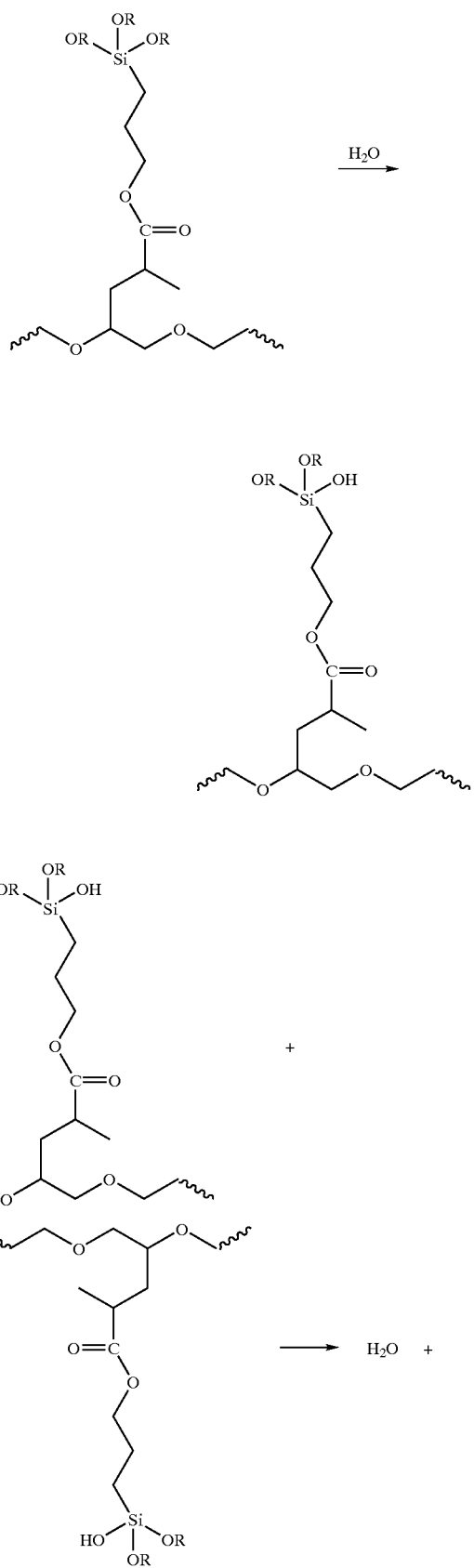

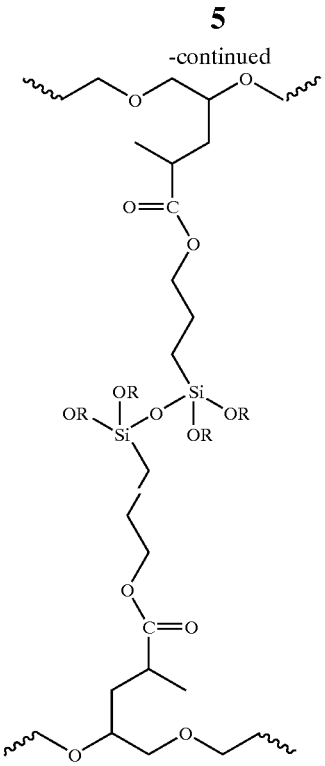

Since crosslinking of the silane graft modified PEO does not normally occur during thermal processing, the graft modified PEO of the present invention provides for more robust thermal processing into functional forms. Furthermore, since the process of forming the silane graft modified PEO of the present invention does not require the use of aqueous solutions, there are no costly and time consuming evaporation steps involved.

The PEO resins useful for graft modification in accordance with the present invention include, but are not limited to, PEO resins having initial reported approximate molecular weights ranging from about 10,000 g/mol to about 8,000,000 g/mol as determined by rheological measurements. Such PEO resins are commercially available from, for example, Union Carbide Corporation having offices in Danbury, Conn., and are sold under the trade designations POLYOX® 205, POLYOX® N-10, POLYOX® N-80. POLYOX® WSR N-750. POLYOX® WSR N-12K and POLYOX® UCARFLOC® Polymer 309.

Fibers, films and foams can be made using conventional processing methods from commercially available PEO resins when modified in accordance with this invention. The PEO resins useful for modification for fiber-making purposes include, but are not limited to, PEO resins having initial reported approximate molecular weights ranging from about 50,000 g/mol to about 400,000 g/mol. Higher molecular weights are desired for increased mechanical and physical properties and lower molecular weights are desired for ease of processing. Desirable PEO resins for fiber making have molecular weights ranging from 50,000 to 300,000 g/mol before modification and more desired PEO resins for fiber making have molecular weights ranging from 50,000 to 200,000 g/mol before modification. The PEO compositions modified from PEO resins within the above resins provide desirable balances between mechanical and physical properties and processing properties. Three PEO resins within the above preferred ranges are commercially available from Union Carbide Corporation and are sold under the trade designations POLYOX® N-750. POLYOX® WSR N-10 and POLYOX® WSR N-80. These three resins have reported approximate molecular weights, as determined by rheological measurements, of about 100,000 g/mol to 300,000 g/mol.

Other PEO resins available from, for example. Union Carbide Corporation, within the above approximate molecular weight ranges are sold under the trade designations WSR N-750, WSR N-3000, WSR-3333, WSR-205, WSR-N-12K, WSR-N-60K, WSR-301, WSR Coagulant, WSR-303. (See POLYOX® Water Soluble Resins, Union Carbide Chemicals & Plastic Company. Inc., 1991 which is incorporated by reference herein in its entirety.) Both PEO powder and pellets of PEO can be used in this invention since the physical form of PEO does not affect its behavior in the melt state for grafting reactions. This invention has been demonstrated by the use of PEO in powder form as supplied by Union Carbide. However, the PEO resins to be modified may be obtained from other suppliers and in other forms, such as pellets. The PEO resins and modified compositions may optionally contain various additives, such as, plasticizers, processing aids, rheology modifiers, antioxidants, UV light stabilizers, pigments, colorants, slip additives, antiblock agents, etc., which may be added before or after modification.

Organic monomers capable of graft polymerization with PEO which monomers contain a trialkoxy silane functional group or a moiety that reacts with water to form a silanol group are useful in the practice of this invention. The trialkoxy silane functional group has the following structure:

$$R_1O-\underset{|}{\underset{Si}{\overset{OR_2}{|}}}-OR_3$$

wherein $R_1$, $R_2$, and $R_3$ are alkyl groups independently having 1 to 6 carbon atoms. The term "monomer(s)" as used herein includes monomers. oligomers, polymers, mixtures of monomers, oligomers and/or polymers, and any other reactive chemical species which is capable of covalent bonding with the parent polymer, PEO. Ethylenically unsaturated monomers containing a trialkoxy silane functional group are appropriate for this invention and are desired. Desired ethylenically unsaturated monomers include acrylates and methacrylates. A particularly desirable ethylenically unsaturated monomer containing a trialkoxy silane functional group is methacryloxypropyl trimethoxy silane. Methacryloxypropyl trimethoxy silane is commercially available from Dow Coming, having offices in Midland, Mich., under the trade designation Z-6030 Silane. Other suitable ethylenically unsaturated monomers containing a trialkoxy silane functional group include, but are not limited to, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethvl dimethoxy silane, and 3-methacryloxypropyl tris(methoxyethoxy) silane.

However, it is contemplated that a wide range of vinyl and acrylic monomers having trialkoxy silane functional groups or a moiety that reacts easily with water to form a silanol group, such as a chlorosilane or an acetoxysilane, provide the desired effects to PEO and are effective monomers for grafting in accordance with the present invention.

The amount of organic monomer having, trialkoxy silane functional groups or silanol-forming functional groups relative to the amount of PEO may range from about 0.1 to about 20 weight percent of monomer to the weight of PEO. Desirably, the amount of monomer should exceed 0.1 weight percent in order sufficiently to improve the processability of the PEO. A range of grafting levels is demonstrated in the Examples. Typically, the monomer addition levels are between about 1.0% and about 15% of the weight of the base PEO resin; particularly, between about 1.0% and about 10% of the weight of the base PEO resin: especially, between about 1.5% and about 5.5% of the weight of the base PEO resin.

A variety of initiators may be useful in the practice of this invention. When grafting is achieved by the application of heat, as in a reactive-extrusion process, it is desirable that the initiator generates free radicals through the application of heat. Such initiators are generally referred to as thermal initiators. For the initiator to function as a useful source of radicals for grafting, the initiator should be commercially and readily available, stable at ambient or refrigerated conditions, and generate radicals at reactive-extrusion temperatures.

Compounds containing an O—O, S—S, or N=N bond may be used as thermal initiators. Compounds containing O—O bonds; i.e., peroxides, are commonly used as initiators for graft polymerization. Such commonly used peroxide initiators include: alkyl, dialkyl, diaryl and arylalkyl peroxides such as cumyl peroxide, t-butyl peroxide, di-t-butyl peroxide, dicumyl peroxide, cuinyl butyl peroxide, 1,1-di-t-butyl peroxy-3,5,5-trimethylcyclohexane, 2,5-dimethyl-2,5-di(t-butylperoxy)hexane, 2,5-dimethyl-2,5-bis(t-butylperoxy)hexyne-3 and bis(a-t-butyl peroxyisopropylbenzene); acyl peroxides such as acetyl peroxides and benzoyl peroxides; hydroperoxides such as cumyl hydroperoxide, t-butyl hydroperoxide, p-methane hydroperoxide, pinane hydroperoxide and cumene hydroperoxide; peresters or peroxyesters such as t-butyl peroxypivalate, t-butyl peroctoate, t-butyl perlenzoate, 2,5-dimethyhexyl-2,5-di(perbenzoate) and t-butyl di(perphthalate); alkylsulfonyl peroxides; dialkyl peroxmonocarbonates; dialkyl peroxydicarbonates; diperoxyketals; ketone peroxides such as cyclobexanone peroxide and methyl ethyl ketone peroxide. Additionally. azo compounds such as 2,2'-azobisisobutyronitrile abbreviated as AIBN. 2,2'-azohis(2,4-dimethylpentanenitrile) and 1,1'-azobis(cyclohexanecarbonitrile) may be used as the initiator. This invention has been demonstrated in the following into Examples by the use of a liquid, organic peroxide initiator available from R. T. Vanderbilt Company. Inc. of Norwalk, Conn., sold under the trade designation VAROX DBPH peroxide which is a free radical initiator and comprises 2,5-bis(tert butylperoxy)-2,5-dimethyl hexane along with smaller amounts of di(tert butylperoxide). Other initiators may also be used, such as LUPERSOL® 101 and LUPERSOL® 130 available from Elf Atochem North America. Inc. of Philadelphia, Pa.

A variety of reaction vessels may be useful in the practice of this invention. The modification of the PEO can be performed in any vessel as long as the necessary mixing of PEO, the monomer and the initiator is achieved and enough thermal energy is provided to affect grafting. Desirably, such vessels include any suitable mixing device, such as Brabender Plasticorders, Haake extruders, Bandbury mixers, single or multiple screw extruders, or any other mechanical mixing devices which can be used to mix, compound, process or fabricate polymers. In a desired embodiment, the reaction device is a counter-rotating twill-screw extruder, such as a Haake extruder available from Haake, 53 West Century Road, Paramus, N.J. 07652 or a co-rotating, twin-screw extruder, such as a ZSK-30 twin-screw, compounding extruder manufactured by Werner & Pfleiderer Corporation of Ramsey, N.J. It should be noted that a variety of extruders may be used to modify the PEO in accordance with the invention provided that mixing and heating occur.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Material

Polyethylene oxide ("PEO"), supplied by Union Carbide under the name POLYOX Water Soluble Resins, was used. POLYOX WSR-205 having a molecular weight of about 600,000 g/mol was used in powder form. The reactive polar vinyl monomer used was 3-(trimethoxysilyl) propyl methacrylate supplied by Aldrich Chemical Company and manufactured by Dow Corning under the trade name, Dow Coming Z-6030 Silane. The peroxide initiator used was Varox DBPH, supplied by R. T. Vanderbilt Company, Inc.

Chemistry

The monomer is composed of two functional groups. The methacrylate function reacts with PEO after a free radical site is initiated with peroxide. The resultant modified PEO resin is still thermally processable as long as it is kept relatively dry. The crosslinking takes place from the other end of the molecule at the alkoxysilane function. The alkoxysilane is readily hydrolyzed into a more reactive silanol and the silanol condenses with another silanol to form a cross-linked network. Because the grafting monomer has three alkoxysilanes, each graft site is theoretical]capable of forming three crosslinks. Use of this type of grafting monomer provides a modified resin, which, while kept relatively dry, can be fabricated into useful structures, and then, when exposed to humid air, become crosslinked. The result is a material that retains the versatility of thermal processability into a variety of structures along with the capability of using those structures for absorbency. This unusual combination of features is available because the crosslinked, hydrophilic network is generated after the structure is fabricated.

Equipment

A bench-scale HAAKE twin-screw extruder was used. This unit contains a set of custom-made, counter-rotating conical twin screws.

Screw Design for the HAAKE Extruder

A general characteristic description is provided in Table 1 since the exact dimensions may be proprietary to the extruder manufacturer.

TABLE 1

| Sections | Descriptions |
| --- | --- |
| Section 1: | A double flighted forward pumping section: Large screw lead (pitch) and a high helix angle |
| Section 2: | A double flighted forward pumping section: Screw pitch is smaller than Section 1 |
| Section 3: | A double flighted forward pumping section: Screw pitch is smaller than Section 2 |
| Section 4: | A double flighted and notched reversed pumping section One complete flight with notches |
| Section 5: | A double flighted notched forward pumping section Two complete flights |
| Section 6: | A double flighted forward pumping section Screw pitch is between sections 1 and 2. |

The die has two openings of 3 mm in diameter, which are separated by 10 mm. The strands were cooled in air and Subsequently pelletized. The feed section was not heated, rather it was cooled by water. The extruder has, three heating sections from the feeding section towards the die designated as Zone 1, Zone 2, and Zone 3. The die was designated as Zone 4.

Reactive Extrusion Process

The first reactive extrusion was done on a HAAKE twin screw extruder of 10/1 L/D with custom designed screws (described above) at a rate of 5 pounds per hour. The pelletized POLYOX 205 was metered into the throat of the extruder at a rate of 37.8 g/min with a K-Tron feeder. In the same manner, Varox DBPH peroxide seas metered at a rate equivalent to 0.25 weight percent of tile POLYOX 205 and the Z-6030 silane was metered in with an Eldex pump at a rate of 2 to 5 weight percent of the POLYOX 205. The temperature profile for the heating zones were 150°, 160°, 160°, and 170° C. The screw speed was 150 rpm. The strands were cooled in air using a fan-cooled conveyer belt. The solidified strands of the grafted POLYOX 205 were then pelletized using a Conair pelletizer.

The sample pellets from this experiment were stored under ambient conditions for four months and then under high humidity (33° C. and 80% relative humidity) for seven days. The resin samples were tested to determine the ultimate gel fraction according to the procedure described below. The gel fraction is the portion of the sample that is cross-linked and no longer soluble in water. The soluble fraction is equal to 1-(gel fraction).

Gel Fraction Test

A sample of film or resin pellet with a weight of 30 to 50 milligrams is weighed in the dry state to the nearest tenth of a milligram. The test sample is place in a 500 ml bottle to which 100 ml of distilled water is added. The bottle is shaken on a laboratory shaker for 30 minutes at room temperature. The contents of the bottle are filtered under vacuum with a Beuchner funnel using Whatman 55 mm filter paper (catalogue # 1001 55) which was pre-dried at 60° C. and weighed to the nearest tenth of a milligram. The insoluble portion of the sample is dried along with the filter paper at 60° C. for two hours and then weighed to determine the dry weight of insoluble material.

Gel fraction or percent gel is taken as the dr weight of recovered (insoluble) material divided by the initial dry weight of the sample. Generally, the average of 5 replicates is reported in Table 2 below:

TABLE 2

| Sample | Weight % Z6030 | Weight % Varox DBPH | Extruder Pressure (psi) | Gel Fraction |
| --- | --- | --- | --- | --- |
| 1-1 | 0 | 0 | 530 | 0 |
| 1-2 | 2 | 0.15 | 330 | 0.91 |
| 1-3 | 5 | 0.25 | 430 | Not tested |

The addition of the monomer and peroxide initiator results in a reduction in extruder pressure compared to the control. The reduced pressure is indicative of reduced melt viscosity. This result indicates that the PEO has been modified into a form that is water-absorbent and not completely water-soluble like the control resin (sample 1-1).

EXAMPLE 2

The following samples were prepared using the same method and extruder temperatures as described above in Example 1 and using the proportions of ingredients indicated in Table 3 below. Since the first sample resulted in low extruder pressure, the temperatures were reduced to bring the extruder pressure into the proper range.

TABLE 3

| Sample | Weight % vinyl triethoxy silane | Weight % Varox DBPH | Extruder pressure (psi) | Comments. Observations |
| --- | --- | --- | --- | --- |
| 2-1-a | 5 | .25 | 92 | Very low pressure, temperatures reduced to 120, 130, 130, 140 |
| 2-1-b | 5 | .25 | 270 | Low melt viscosity |
| 2-2 | 2 | .15 | 350 | Slight pressure increase |
| 2-3 | 0 | 0 | 700 | P205 control, high pressure, rough strands |

Pellets from samples 2-1-b, 2-2 and 2-3 were stored for approximately ten weeks under laboratory conditions, exposed to ambient humidity. All three samples aged under these conditions, dissolved in water after standing overnight.

The resin samples prepared with triethoxy vinyl silane remained water-soluble. This result suggests that this monomer was not grafted onto P205 under the same conditions that were effective for grafting Z6030. The significant reduction in melt pressure and melt viscosity indicates that chain scission of the PEO was occurring rather than grafting. Different conditions or initiators may be needed to induce grafting between PEO and triethoxy vinyl silane.

EXAMPLE 3

A third reactive extrusion experiment was conducted to evaluate the effect of higher addition level of the Z6030 monomer along with proportionately higher addition of the peroxide initiator. The same screw design and production rate as EXAMPLE 1 was used. The pelletized POLYOX 205 was metered into the throat of the extruder at a rate of 37.8 g/minute with a K-Tron feeder. Dow Corning Z-6030 Silane was metered into the throat of the extruder with an Eldex pump at a rate of 3.78 g/minute, equivalent to ten weight percent of the POLYOX 205. In the same manner, Varox DBPH peroxide was metered at a rate equivalent to 0.40 weight percent of the POLYOX 205. A second code was run at five weight percent addition of Z6030 with Varox DBPH peroxide metered at a rate equivalent to 0.33 weight percent of the POLYOX 205. The temperature profile for the heating zones were 150°, 160°, 160°, and 170° C. The strands were cooled in air using a fan-cooler conveyor belt. The solidified strands of the grafted POLYOX 205 were then pelletized on a Conair pelletizer.

The sample descriptions and gel fraction results are shown in the Table 4 below. These gel fraction results were obtained after six months at ambient conditions followed by one week at 80% relative humidity.

TABLE 4

| Sample | Weight % Z6030 | Weight % Varox DBPH | Extruder pressure (psi) | Gel Fraction |
|---|---|---|---|---|
| 3-1 | 10 | .40 | 420 | .92 |
| 3-2 | 5 | .33 | 450 | .95 |

This result indicates that five percent Z6030 is sufficient monomer to provide a nearly fully crosslinked, PEO gel.

EXAMPLE 4

The Z6030 reactive grafting was done with a ZSK-30 extruder. A ZSK-30 co-rotating, twin-screw extruder (manufactured by Werner & Pfleiderer) with 14 barrel sections and 1338 nun total processing section length was used. The first barrel was not heated, but cooled by water. The peroxide was injected into barrel #5 and the Z6030 monomer was injected into barrel #6. Both chemicals were injected via a pressurized nozzle injector. The die has four openings of 3 mm in diameter, which are separated by 7 mm. Polymer strands were extruded onto an air-cooling belt and subsequently pelletized.

The following extruder barrel temperatures (in ° C.) were set to the following levels during the extrusion as shown in Table 5:

TABLE 5

| Zone 1 | Zone 2 | Zone 3 | Zone 4 | Zone 5 |
|---|---|---|---|---|
| 166° | 180° | 180° | 180° | 180° |

The polymer melt temperature was 195–205° C. The polymer strands were cooled on a stainless steel cooling belt and subsequently pelletized.

TABLE 6

ZSK-30 Screw Configuration for Reactive Extrusion

| Element No. | Description | Element No. | Description |
|---|---|---|---|
| 1 | PKR 10 | 31 | KB45/5/14 |
| 2 | 20/10 | 32 | KB45/5/14 |
| 3 | 42/42 | 33 | 20/20 |
| 4 | 42/42 | 34 | 20/20 |
| 5 | 28/28 | 35 | 20/20 |
| 6 | 28/28 | 36 | 28/28 |
| 7 | 20/20 | 37 | 28/28 |
| 8 | 20/20 | 38 | 28/28 |
| 9 | KB45/5/28 | 39 | 20/20 |
| 10 | KB45/5/14 | 40 | 20/10 LH |
| 11 | 28/28 | 41 | 42/42 SK |
| 12 | 28/28 | 42 | 42/42 SK |
| 13 | 28/28 | 43 | 42/42 |
| 14 | 28/28 | 44 | 20/20 |
| 15 | 20/20 | 45 | 20/20 |
| 16 | 28/28 | 46 | 20/20 |
| 17 | 28/28 | 47 | 20/20 |
| 18 | 20/20 | 48 | 20/20 |
| 19 | KB45/5/42 | 49 | 20/20 |
| 20 | 28/28 | 50 | 20/20 |
| 21 | 20/20 | 51 | 20/20 |
| 22 | KB45/5/28 | 52 | 20/20 |
| 23 | KB45/5/14 LH | 53 | 20/10 |
| 24 | 28/28 | 54 | 20/10 |
| 25 | 20/20 | 55 | 20/10 |
| 26 | 20/20 | 56 | 20/10 |
| 27 | 28/28 | 57 | 20/10 |
| 28 | 28/28 | 58 | 20/10 |
| 29 | 20/20 | 59 | 20/10 |
| 30 | 20/20 | 60 | 14/14 |

The PEO powder resin was fed into the ZSK-30 extruder with a K-Tron volumetric feeder at a throughput of 20 lbs/hr. The modified PEO strands were cooled between stainless steel belts that were cooled with water from the opposite side followed by pelletization.

The results are shown in Table 7 below:

TABLE 7

| Sample | Weight % Z6030 | Weight % Varox DBPH | Extruder pressure (psi)/% torque/melt temperature ° C. | Gel Fraction |
|---|---|---|---|---|
| 4-1 | 5.6 | .165 | 320/46%/214 | .94 |
| 4-2 | 5.6 | .33 | 320/46%/216 | Not tested |
| 4-3 | 11.3 | .33 | 380/47%/218 | Not tested |
| 4-4 | 11.3 | .66 | 390/48%/216 | .96 |

The variation in monomer and peroxide levels had minimal effect on the process data for pressure and torque. Gel fraction for samples 4-1 and 4-4 was tested after four months at ambient temperature and humidity and one week at elevated humidity and temperature (33° C. and 89% relative humidity).

EXAMPLE 5

Another reactive extrusion run on the ZSK-30 was designed to determine the effect of peroxide initiator addition and screw rpm, which determines residence time for the reaction, upon the resin properties. The silane monomer addition level was held constant at 1.3 mole percent (based on moles of ethylene oxide repeat) or 7.3 weight percent. The standard settings for temperature were the same as described in Example 4.

The settings for the experimental variables and the process data collected during the experiment are shown in Table 8, below.

TABLE 8

Variable Settings and Process Data

| Run # | VARIABLE Rpm | SETTINGS Wt. % Peroxide | PROCESS Melt Temp(° C.) | RESPONSE Percent of maximum Torque | DATA Melt Pressure |
|---|---|---|---|---|---|
| 5-1 | 300 | 0.22 | 210 | 45 | 600 |
| 5-2 | 100 | 0.22 | 200 | 85 | 810 |
| 5-3 | 100 | 0.13 | 200 | 86 | 830 |
| 5-4 | 300 | 0.13 | 205 | 42 | 700 |
| 5-5 | 200 | 0.17 | 205 | 50 | 800 |
| 5-6 | 100 | 0.13 | 201 | 86 | 890 |
| 5-7 | 300 | 0.13 | 206 | 43 | 700 |
| 5-8 | 300 | 0.22 | 206 | 42 | 600 |
| 5-9 | 100 | 0.22 | 199 | 85 | 780 |

The process data in Table 8 indicates a significant effect of the screw rpm upon the torque. Note that a reduction in rpm from 300 to 100 results in the torque readings increasing to nearly double. A significant, but less dramatic increase is observed in the melt pressure at the reduced rpm setting. Changes in the peroxide addition level had minimal effect on torque or pressure within the range studied.

Gel Fraction Results

Gel fraction results 165 hours cure at 33° C. and 80% relative humidity are shown in Table 9 below:

TABLE 9

| Resin Sample | rpm | Weight % Varox DBPH | Gel Fraction |
|---|---|---|---|
| 5-6 | 100 | 0.13 | 0.87 |
| 5-7 | 200 | 0.13 | 0.82 |
| 5-8 | 300 | 0.22 | 0.84 |
| 5-9 | 100 | 0.22 | 0.85 |

EXAMPLE 6

To provide a modified PEO resin suitable for fiber spinning, a lower molecular weight PEO. POLYOX N-80, was used as the starting resin for reactive grafting on the ZSK-30 extruder. The initial molecular weight of this resin was 200,000 g/mol. Temperature settings for the extruder were the same as Examples 4 and 5. Other process settings are shown in the Table 10 below.

TABLE 10

| Resin Sample | Wt % Z6030 | Wt % Varox DBPH | rpm | Process Data Pressure/torque | Gel Fraction |
|---|---|---|---|---|---|
| 6-1 | 7.3 | 0.17 | 200 | 190/59 | 0.62 |

The lower molecular weight PEO results in lower extruder pressure compared to the POLYOX 205.

In the examples that follow, the modified PEO resin was converted into film within one or two days of preparation so that the resin would still be in an uncrosslinked state.

For film processing, a Haake counter-rotating, twin-screw extruder was used with a 4 inch slit die attached. A chilled wind-up roll maintained at 15°–20° C. was used to collect the film. The temperature profile for the four heating zones was 170°, 180°, 180° and 190° C. Screw speed and wind-up speed were adjusted such that the film thickness was 2 to 3 mil. The process was allowed to stabilize before the film was collected. Film samples were tested for gel fraction according to the test method previously described. In addition, the films were tested for fluid absorbency (grain per gram uptake) under unrestrained swelling conditions according to the following test method.

Gram per Gram Uptake (Free Swell)

A sample of film or resin pellet with a weight of 30 to 50 milligrams is weighed in the dry state to the nearest tenth of a milligram. The test sample is place in a 500 ml bottle to Which 100 ml of distilled water is added. The bottle is shaken on a laboratory shaker for 3 minutes at room temperature. The contents of the bottle are filtered under vacuum with a Beuchner funnel using Whatman 55 mm filter paper. The swollen sample is removed from the filter paper and weighed to the nearest milligram.

Gram per grant uptake is calculated as the wet weight of recovered (insoluble) material, divided by the initial dry weight of the sample, minus 1. Generally, the average of 5 replicates is reported. A similar procedure is used with 0.9% saline replacing distilled water.

Films from Examples 1 and 2 were conditioned in a high humidity environment (80% relative humidity at 33° C.) for 16 hours. Four film samples were cut and weighed: 50% silane (dry film), 5% silane (humidity conditioned), 2% silane (dry film), 2% silane (humidity conditioned). The films were place in a vial of 20 ml of 0.9% saline and kept at 35 C. After 16 hours in a free swell condition, the liquid was poured off and the gel isolated, blotted to remove surface moisture, and weighed. Gram per gram uptake under these conditions is shown in Table 11 below.

TABLE 11

| Film Sample | Resin Source | Description | Ambient Condition Uptake | Humidified Condition Uptake |
|---|---|---|---|---|
| 7-2 | 1-2 | 2% Z6030 | 3 g/g | 9 g/g |
| 7-3 | 1-3 | 5% Z6030 | 23 g/g | 20 g/g |
| 7-4 | 2-1-b | 5% vinyl silane | Dissolved | Dissolved |
| 7-5 | 2-2 | 2% vinyl silane | Dissolved | Dissolved |

These initial results indicate the high absorbency of modified PEO resins when they are successfully grafted and allowed to crosslink. However, if grafting is not successful, as in samples 7-4 and 7-5, the film responds to saline much like unmodified PEO and dissolves.

Uptake of Simulated Mensers

Since PEO crosslinked by other means was previously known to be an effective absorbent for menses, films from this extrusion experiment were also tested for absorbency with simulated menses.

Films samples (1.5"×1.5"), prepared from POLYOX 205 grafted with five percent Z6030, were soaked in 20 ml of menses simulant composed of swine blood of controlled hemocrit with albumin added to simulate the visco-elastic properties of menses. The samples were soaked for 30 minutes, removed, the excess fluid was drained from the surface, and then weighed. This weight is used to calculate the saturated uptake. The sample is then placed under pressure of 0.5 psi and then weighed again to determine the blotted uptake. The results are shown below in Table 12:

TABLE 12

| Sample | Saturated Uptake (g/g) | Blotted Uptake (g/g) |
|---|---|---|
| 5% Z6030, ambient (for 2 months) | 21 | 10 |
| 5% Z6030, humidified 24 hr. | 13 | 10 |

Thermal Analysis

Table 13 below contains the differential scanning calorimeter ("DSC") results for the Z6030 grafted POLYOX 205 in comparison to the ungrafted resin. Both the heating and the cooling rates were 20° C. per minute. There are several notable differences in the grafted polymer compared to the ungrafted P205.

1. There is a significant increase in the crystallization temperature (Tc) for the ,rafted resins. (~40° C. for the ungrafted resin compared to ~47° C. for the grafted).
2. Based on the second heat cycle (which erases prior heat history effects) the grafted resins appear to have a lower melt temperature and a slightly higher glass transition temperature ($T_g$) compared to the unmodified resin.

TABLE 13

Initial Thermal Analysis Results

| | POLYOX 205 (unmodified) | 2% Z6030 | Humidified Condition | 5% Z6030 | Humidified Condition |
|---|---|---|---|---|---|
| Film resin source | 1-1 | 1-2 | 1-2 | 1-3 | 1-3 |
| 1st heat Tg (C) | −55.7 | −52.2 | −54 | −55.5 | −54.5 |
| Tm (onset/peak) | 60.4/71.3 | 56.8/62.6 | 60.6/67.2 | 56/61.7 | 58.7/66.1 |
| heat of fusion | 126 | 124 | 166 | 139 | 162 |
| estimated crystallinity (100% = 213 J/g) | 59% | 58% | 78% | 65% | 76% |
| Tc (onset/peak) | 47/39.8 | 49.3/46 | 50/47.9 | 49.4/47 | 50/48.7 |
| heat of fusion | 114 | 116 | 134 | 130 | 126 |
| estimated crystallinity (100% = 213) | 54% | 54% | 63% | 61% | 59% |
| 2nd heat Tg | −55.6 | −46 | | −50.5 | |
| 2nd heat Tm (onset/peak) | 60.5/71.3 | 59.2/64.7 | 58.6/64.4 | 58.1/63.9 | 57.9/63.4 |
| heat of fusion | 122 | 122 | 139 | 136 | 140 |
| estimated crystallinity (100% = 213) | 57% | 57% | 65% | 64% | 66% |

Film Properties

Film properties for the Z6030 grafted POLYOX 205 are shown in Table 14 below for both ambient conditions and humidified film. For the sake of comparison, the properties of POLYOX 205 grafted with hydroxyethyl methacrylate ("HEMA") are also shown. In general, the ambient films have similar properties to the HEMA grafted film, particularly low modulus, high break stress, and high elongation at break. The most notable change for films that have been conditioned under high humidity) to induce crosslinking is an increase in the film modulus.

TABLE 14

Film Properties from Initial Extrusion Experiment

| Film Resin Source | Film Orientation | Thickness (mils) | Break Stress (Mpa) | % Strain a, break | Modulus (Mpa) | Energy to Break (J/cc) |
|---|---|---|---|---|---|---|
| 1-3 | MD | 3.18 | 22.2 | 1075 | 103 | 159 |
| 1-3 | MD | 3.13 | 23.4 | 1132 | 146 | 179 |
| 1-2 | MD | 2.98 | 14.2 | 843 | 162 | 105 |
| 1-2 | MD | 2.96 | 13.7 | 592 | 226 | 75 |
| 205 grafted with 1.5% HEMA | MD | 1.16 | 25.4 | 1153 | 163 | 174 |

Grating POLYOX 205 with Z6030 silane provides for a crosslinkable structure with good absorbency for water, saline, and simulated menses. The excellent dry film properties previously obtained with grafted PEO are retained when Z6030 is used as the grafting monomer. All films prepared with triethoxy vinyl silane remained water-soluble.

EXAMPLE 7

Another extrusion experiment was run as a control experiment without the addition of the peroxide initiator to confirm the graft chemistry described above. Without the peroxide initiator, the resulting material would be a blend of PEO and the Z-6030 monomer rather than a grafted copolymer.

Pelletized POLYOX 205 was metered into the throat of the Haake extruder as described above at a rate of 37.8 g/min with a K-Tron feeder. Methacryloxypropyl silane (Dow Corning Z-6030 Silane) was metered into the throat of the extruder with an Eldex pump at a rate of 3.78 g/min, equivalent to ten weight percent of the POLYOX 205. The temperature profile for the heating zones was 150°, 160°, 160°, and 170° C. The resultant strands were cooled in air using a fan-cooler conveyer belt. And the solidified strands of the grafted POLYOX 205 were then pelletized on a Conair pelletizer. A film was cast with a thickness of about 3 mils (0.76 mm).

Gel Fraction

A film sample from this experiment was conditioned at 37° C. and 80% relative humidity for 7 days. Gel fraction testing using the procedure described above resulted in gel content of less than two percent. In contrast, when the initiator is included to promote grafting of the alkoxysilane onto the PEO; the gel fraction under similar conditioning is typically more than 60 percent even with a shorter time of humidification.

EXAMPLE 8

Films were prepared from the modified PEO resins of Example 4 and the mechanical properties of the dry film were tested. The MD film properties in the dry state are shown in Table 15 below. The changes in properties that result from the formation of crosslinks under the curing condition are evident. For this table, the cure condition was 92 hours at 37° C. and 80% relative humidity.

TABLE 15

Film Properties as a Function of Cure

| Sample MD Film Properties | Break stress (Mpa) | | % Strain @ break | | Modulus (Mpa) | | Energy to Break (J/cc) | |
|---|---|---|---|---|---|---|---|---|
| | Uncross-linked | cross-linked | Uncross-linked | cross-linked | Uncross-linked | cross-linked | Uncross-linked | cross-linked |
| Film 8-1 (Resin 4-1): 5.6% Z6030 .16% peroxide | 21.8 | 30.6 | 942 | 1127 | 143 | 192 | 136 | 213 |
| Film 8-2 (Resin 4-2): 5.6% Z6030 .33% peroxide | 20.9 | 25.9 | 1158 | 1084 | 132 | 177 | 156 | 177 |
| Film 8-3 (Resin 4-3): 11.2% Z6030 .33% peroxide | 19.5 | 27.7 | 1034 | 1105 | 111 | 173 | 132 | 188 |
| Film 8-4 (Resin 4-4): 11.2% Z6030 .66% peroxide | 19.8 | 25.3 | 1052 | 1008 | 133 | 190 | 137 | 167 |

As the results indicate, crosslinking provides for improved film properties. Significant improvements are evident for break stress and energy to break. An increase in modulus is also evident, but the modulus does not increase to levels that are much different from HEMA-grafted PEO, with a modulus of about 165 Mpa. The high strain at break is not negatively impacted by the crosslinking reaction.

EXAMPLE 9

Films were prepared from the modified PEO resins of Example 5.

Gel fraction results after 26 and 165 hours at 33° C. and 89% relative humidity are shown in Table 16 below, along with results for gram-per-gram uptake of 0.9% saline.

TABLE 16

| Film | Resin Source | RPM | Wt. % Peroxide | 26 hour gel fraction | 165 hour gel fraction | 165 hour g/g uptake |
|---|---|---|---|---|---|---|
| 9-1 | 5-1 | 300 | .22 | 40 | 68 | 19.4 |
| 9-2 | 5-8 | 300 | .22 | 18 | 58 | 16.9 |
| 9-3 | 5-2 | 100 | .22 | 68 | 74 | 17.6 |
| 9-4 | 5-9 | 100 | .22 | 57 | 80 | 14.2 |
| 9-5 | 5-4 | 300 | .13 | Not tested | 50 | 22.2 |
| 9-6 | 5-7 | 300 | .13 | 14 | 65 | 21.2 |
| 9-7 | 5-3 | 100 | .13 | 77 | 83 | 19.3 |
| 9-8 | 5-6 | 100 | .13 | 81 | 75 | 14.8 |
| 9-9 | 5-5 | 200 | .17 | 79 | 84 | 13.7 |

The results indicate a significant effect of screw rpm and a minimal effect of peroxide level. Note that low screw rpm, which results in a longer residence time, produces a greater gel fraction, presumably as a result of higher grafting.

In general, the data from the extended cure time follows the same pattern observed after 26 hours of cure. The screw rpm (residence time) had the largest impact, while the peroxide level had little effect. Note that there is an overall increase in the gel fraction with the additional cure time.

The results for g/g uptake suggest that the capacity of the crosslinked PEO is increased with a lower level of crosslinking. This inverse relationship between capacity and crosslink concentration is consistent with the trends observed with polyacrylate super absorbents and also with PEO crosslinked with urethanes. The results also suggest that lower levels of the Z6030 crosslinking monomer under reactive grafting conditions that promote high grafting efficiency could provide for higher capacity at a lower cost. Therefore, for certain applications it is desirable that the polymer have a level of gel formation of about 2%–3% by weight desirably, at least about 2% by weight. Such low levels of crosslinking may also be used to produce a polymer that has delayed water solubility or dissolution.

However, this uptake data is obtained under free swell conditions. For absorbency under load (AUL), a higher crosslink density may he needed. Therefore, for other applications it is desirable that the polymer have a level of gel formation of up to about 98% by weight. For other applications, it may be desirable to have a level of gel formation of about 50%–60% by weight.

An even more ideal structure would be similar to the shell crosslinked polyacrylates. This gradient in crosslinking might be achieved by surface application of a catalyst for the crosslinking reaction. Such a product would have a higher degree of crosslinking on the surface and a lower degree of crosslinking in the interior. Therefore, for certain applications it is desirable to have a level of gel formation of about 2% to about 60% by weight, and for other applications a level of gel formation of about 50% to about 98% by weight. The ability to vary the amount of gel formation provides the ability to select the properties that are desired in the final product.

EXAMPLE 10

Gel Fraction Under Ambient Aging Conditions

Film samples were stored in plastic bags under ambient laboratory conditions of temperature and the humidity available within the plastic bag. These conditions simulate the exposure conditions for films fabricated into a component of a personal care product that is packaged in a plastic bag. As shown in Table 17 below, the alkoxysilane grafted PEO crosslinks slowly under these storage conditions.

TABLE 17

| Sample Description | Resin Source | Storage Time | Gel Fraction |
|---|---|---|---|
| 5% Z6030 .33% peroxide | 3-2 | 4 weeks | 32% |
| 5% Z6030 0.25% peroxide | 1-3 | 8 weeks | 52% |
| 5% Z6030 .33% peroxide | 3-2 | 18 weeks | 69% |
| 10% Z6030 .40% peroxide | 3-1 | 18 weeks | 70% |

EXAMPLE 11

Addition of Catalyst to Accelerate Crosslinking Reaction

The results obtained for samples prepared up to this time appeared to become fully crosslinked after about 7 days at elevated humidity and within 18 weeks under ambient, packaged storage conditions. Based on these results it is apparent that it may be even more desirable to create a crosslinked structure without exposure to high humidity or to require extended storage at ambient conditions. This objective could be met if a catalyst for the crosslinking reaction could be identified which could be added just prior to fabrication into the final structure. The catalyst should accelerate the crosslinking reaction so that crosslinking of the structure occurs under ambient storage conditions within the normal lag time between manufacturing and usage.

Resin pellets obtained from the second factorial experiment on the ZSK-30 PEO (POLYOX 205 reactively grafted with 7.3 weight percent Z6030) was coated with various levels of stearic acid by shaking the pellets and the stearic acid powder together in a plastic bag. Since there was not enough of any single sample to conduct the catalyst study, a composite sample was prepared by blending Samples 1–9 into a single "average" composition. Addition levels of stearic acid were 0, 0.1, 0.2, 0.4, 0.6 and 0.8 weight percent. The blends with stearic acid were prepared within four days of the reactive extrusion to minimize crosslinking during storage. Each blend was cast into a film using the HAAKE extruder under the conditions described above.

Film Observations and Gel Fraction

TABLE 18

| Stearic Acid Level | Film Casting Observations | Gel Fraction after 1 day of ambient storage |
|---|---|---|
| 0 | Smooth, thin film | 60% |
| 0.1 | Smooth, thin film | 55% |
| 0.2 | Smooth, thin film, slight torque increase | 47% |
| 0.4 | Smooth film, slightly thicker, higher torque | 81% |
| 0.8 | Rough film, thicker, higher torque | 96% |

The results above are somewhat obscured by the fact that the resin with no stearic acid added had a high gel fraction. (The gel fraction testing of Samples 1–9, which were combined for this study, was completed after the catalyst study). Nevertheless, the results indicate that addition of stearic acid at a level of at least 0.4%, is effective at increasing the gel fraction after just one day of storage under ambient conditions. However, the results also indicate that addition of excessive stearic acid causes difficulty in fabricating the resin into final form, presumably from premature crosslinking inside the extruder.

EXAMPLE 12

The resin from Example 6 (sample 6-1) was used to prepare monofilaments on a pilot-scale fiber spinning line. The spinning line consisted of two ¾ inch diameter 24:1l:d (length:diameter) extruders with three heating zones which feed into a spin pump, through a ¾ Koch SMX static mixer unit and then into a spinpack, from which the monocomponent fibers were spun. The spinpack had 15 holes of 0.5 mm diameter.

The monofilament fibers were processed using the one extruder with a temperature profile of 170° C., 175° C., 180° C., 180° C., 180° C., 185° C., 185° C., for zones 1 through 3, melt pump, mixer and spinpack. The fibers ere quenched at ~26° C. and collected in a freefall state (without draw down by a draw roll). The fibers were collected onto a spindle for testing.

Fiber samples were exposed to humid air (37° C. and 80% relative humidity) for one week and then tested for gel fraction according to the test method previously described. The fibers were found to have a gel fraction of 57% and absorbed 21 grams of water per gram of fiber.

The fibers displayed significant swelling in water. Fibers were cut to 25 mm in length and found to have a diameter of 0.38 mm in the dry state. After 30 minutes of immersion in water at room temperature, the fibers swelled to a length of 57 mm and the diameter increased to 2.0 mm. The dimensional changes observed were a length increase of 2.25 times the original length and an increase in diameter of 5.2 times the diameter of the dry fiber.

The series of foregoing Examples indicates that the material of the present invention has a unique combination of attributes: good absorbency for water, urine, and menses along with the capability to fabricate a wide range of structures using thermal processing. The ability to generate structures in a latent form (uncrosslinked) via melt processing coupled with a facile method to induce crosslininking into an absorbent material is very rare.

The absorbency properties of this new material are at an intermediate level between polyacrylate superabsorbents and cellulose pulp as shown in Table 19 below.

TABLE 19

| Comparative Absorbent Properties | Cross-linked PEO | Polyacrylate superabsorbent | Cellulose pulp |
|---|---|---|---|
| Free swell absorbency | 12–25 g/g | 26–39 g/g | 3–6 g/g |
| Absorbency under 0.5 psi load | 8–14 g/g | 20–30 g/g | 2 g/g |

Another beneficial property provided by using PEO as a starting polymer is a low glass transition temperature. This attribute is particularly beneficial for personal care or medical products because the structures made from this material are soft and flexible—much like polyethylene or polypropylene which is commonly used to fabricate products in these markets. Plastic-like mechanical and fabrication properties along with good absorbency make this material highly unique. Some potential uses of the present invention are described below.

It is at the level of fabricated structures that the thermoplastic processability of the present invention opens up a wide range of potential structures. The present application describes simple films with good dry properties and high absorbency. When these films are placed in contact with fluid, they swell significantly (by a factor of about three times the original cross-machine direction). In addition, the films upon absorbing fluid are transformed from a plastic film to an even softer more compliant and unexpectedly elastomeric material.

Film applications are not limited to monolayer films. Also anticipated are multi-layer films (coextruded or microlayers). Films may be filled with particulate, such as polyacrylate superabsorbent particles, or mineral fillers, such as clay. The forms described may also be applied to blends composed of alkoxysilane-grafted PEO with other polymers. Also, a wide variety of laminated structures are possible. For example, films may be laminated with nonwoven structures, such as meltblown or spunbond. Laminates are possible with tissue webs or woven fabrics. Specifically, a layer of film in accordance with the present invention can be laminated between two nonwoven layers, such as sheets of tissue. Fibers in accordance with the present invention may be laminated with other structures or with other fibers made from the same or different material, such as pulp. Fibers can be laminated with films of the same or different material. Because the alkoxysilane-grafted PEO has a rather low melting point, the laminates may be fabricated by melt extrusion onto the other component or by applying pressure to both components as they passes through heated nips.

Because of the thermal processability of alkoxysilane-grafted PEO, the present invention may be used for fabricating foam structures. Thermally processed foam technology is widely practiced with polyethylene by utilizing chemical and physical blowing agents. Alkoxysilane-grafted PEO has properties similar to polyethylene so it is contemplated that the use of chemical blowing agents will also produce foam structures. However, unlike polyethylene foams, the foams made from alkoxysilane-grafted PEO should be highly absorbent. Extension of the foam technology to produce net-like structures is also anticipated. Laminates can also be formed from foam structures. Specifically, foams in accordance with the present invention can be laminated with films of the same or different materials.

It is expected that fibrous structures can be fabricated with the alkoxysilane-grafted PEO. Such fibrous structures include melt blown and spunbond nonwovens, as well as bicomponent fibers and structures made from them. Filaments that swell and become elastomeric when contacted with fluid are possible.

The compositions of the present invention can also function as an adhesive. For example, a first material may be adhered to a second material by interposing between the first and second materials and in contact therewith a melt processed poly(ethylene oxide) having graft polymerized thereto an organic moiety including a trialkoxy silane functional group or a moiety that reacts with water to form a silanol group at an elevated temperature, and permitting the melt processed material to cool to ambient temperature.

With this wide range of potential structures, and the product uses for alkoxysilane-grafted PEO are enormous. Articles that are made by injection molding, blow molding, or thermoforming can also be made from alkoxysilane-grafted PEO. Within the personal care market, the present invention is well-suited for a thin, elastomeric film for urine or menses absorption. Alkoxysilane-grafted PEO may also be used as a wound dressing to absorb wound exudate. Laminates prepared from this material may also be used as absorbent bed pads.

The change in properties upon contact with fluid from a plastic to an elastomeric material indicates a relaxation process within the structure that may be utilized for controlled release of beneficial agents. Another application is an implantable material to prevent surgical adhesions. The anti-adhesion properties of PEO are well documented. This property of PEO combined with the capability of alkoxysilane-grafted PEO to form an insoluble gel structure when exposed to fluid may provide the combination of properties to solve the significant problem of surgical adhesions.

The properties of alkoxysilane-grafted PEO in the gel state have not been extensively investigated. However, because it does form an easily processable fluid-filled gel it may be used as a conductive material for detection electrodes or as a conducting medium for polymer batteries. In addition, there is good potential that alkoxysilane-grafted PEO may function as an effective chromatographic medium in the gel state.

The present invention has been illustrated in great detail by the above specific Examples. It is to be understood that these Examples are illustrative embodiments and that this invention is not to be limited by any of the Examples or details in the Description. Those skilled in the art will recognize that the present invention is capable of many modifications and variations without departing from the scope of the invention. Accordingly, the Detailed Description and Examples are meant to be illustrative and are not meant to limit in any manner the scope of the invention as set forth in the following claims. Rather, the claims appended hereto are to be construed broadly within the scope and spirit of the invention.

What is claim is:

1. A method comprising exposing to moisture an article made from poly(ethylene oxide) having graft polymerized thereto an organic moiety including a trialkoxy silane functional group or a moiety that reacts with water to form a silanol group, such that said graft polymerized poly(ethylene oxide) at least partially crosslinks and is capable of absorbing a quantity of aqueous liquid, wherein the article is selected from the group consisting of a film, a fiber, a foam, and a pellet.

2. A fiber made from melt processed poly(ethylene oxide) having graft polymerized thereto an organic moiety including a trialkoxy silane functional group or a moiety that reacts with water to form a silanol group.

3. A film made from melt processed poly(ethylene oxide) having graft polymerized thereto an organic moiety including a trialkoxy silane functional group or a moiety that reacts with water to form a silanol group.

4. A foam made from melt processed poly(ethylene oxide) having graft polymerized thereto an organic moiety including a trialkoxy silane functional group or a moiety that reacts with water to form a silanol group.

5. A pellet made from melt processed poly(ethylene oxide) having graft polymerized thereto an organic moiety including a trialkoxy silane functional group or a moiety that reacts with water to form a silanol group.

6. A method comprising:
combining poly(ethylene oxide), an initiator and an organic monomer capable of graft polymerization with said poly(ethylene oxide), said organic monomer including a trialkoxy silane functional group or a moiety that reacts with water to form a silanol group;
subjecting the combination of poly(ethylene oxide), the initiator and organic monomer to conditions sufficient to graft the organic monomer onto the poly(ethylene oxide);
melt processing the grafted polymer into a functional form; and
subjecting the functional form to humid conditions sufficient to induce at least partial crosslinking of the polymer.

7. A laminated structure comprising a first layer comprising melt processed poly(ethylene oxide) having graft polymerized thereto an organic moiety including a trialkoxy silane functional group or a moiety that reacts with water to form a silanol group laminated to a second layer.

8. The laminated structure of claim 7, wherein said first layer is a fiber, a film or a foam.

9. The laminated structure of claim 7, wherein said second layer comprises melt processed poly(ethylene oxide) having graft polymerized thereto an organic moiety including a trialkoxy silane functional group or a moiety that reacts with water to form a silanol group.

10. The laminated structure of claim 9, wherein said second layer is a fiber, a film or a foam.

11. The laminated structure of claim 9, wherein said second layer comprises a nonwoven layer.

12. The laminated structure of claim 7, wherein said second layer comprises a nonwoven layer.

13. The laminated structure of claim 7, wherein said second layer comprises wood pulp.

14. The laminated structure of claim 7 further comprising a third layer laminated to said first layer.

15. The laminated structure of claim 7, wherein said first layer is a film and said second and third layers comprise sheets of nonwoven material.

16. The laminated structure of claim 15, wherein said nonwoven material is tissue.

17. A method of adhering a first material to a second material comprising
a. interposing between said first and second materials and in contact therewith at an elevated temperature an adhesive comprising a melt processed Poly(ethylene oxide) having graft polymerized thereto an organic moiety including a trialkoxy silane functional group or a moiety that reacts with water to form a silanol group, and
b. permitting said melt processed material to cool to ambient temperature.

18. A method comprising exposing to moisture an article made from poly(ethylene oxide) having graft polymerized thereto an organic moiety including a trialkoxy silane functional group or a moiety that reacts with water to form a silanol group, such that at least a portion of said graft polymerized poly(ethylene oxide) crosslinks and absorbs at least a portion of an aqueous liquid, whereby at least a portion of said graft polymerized poly(ethylene oxide) forms a non-water soluble gel.

19. The method of claim 18, wherein said gel fraction comprises up to about 98% by weight.

20. The method of claim 18, wherein said gel fraction comprises about 2% by weight.

21. The method of claim 18, wherein said gel fraction comprises about 2%–98% by weight.

22. The method of claim 18, wherein said gel fraction comprises about 2%–60% by weight.

23. The method of claim 18, wherein said gel fraction comprises about 50%–60% by weight.

24. The method of claim 18, wherein said gel fraction comprises about 50%–98% by weight.

* * * * *